(12) United States Patent
Murata et al.

(10) Patent No.: US 6,441,040 B1
(45) Date of Patent: *Aug. 27, 2002

(54) ORAL PREPARATIONS COMPRISING S-(3-HYDROXYPROPYL)-L-CYSTEINE

(75) Inventors: Misao Murata; Yukihiro Saito; Hideyoshi Kanbe; Shuji Yamauchi; Akira Iwasa, all of Chiba (JP)

(73) Assignee: SSP Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/176,155

(22) Filed: Oct. 21, 1998

(51) Int. Cl.$^7$ .................. A61K 31/195; A61K 31/718; A61K 31/724; C07C 317/02
(52) U.S. Cl. ....................... 514/562; 514/58; 514/60; 562/556
(58) Field of Search ............................ 514/562, 58, 60; 562/556

(56) References Cited

U.S. PATENT DOCUMENTS 5,614,197 A * 3/1997 Pathak et al. ............ 424/195.1
5,626,837 A * 5/1997 Shimada et al.
5,846,562 A * 12/1998 Yanai et al. ................. 424/451

FOREIGN PATENT DOCUMENTS

| EP | 0 209 957 A1 | * 7/1986 | ......... A61K/31/195 |
| EP | 0 346 882 A2 | 12/1989 | ....... C07C/149/247 |
| EP | 0 346 883 A2 | 12/1989 | ......... A61K/31/195 |
| FR | 72.21606 | 1/1974 | ......... A61K/27/00 |

* cited by examiner

Primary Examiner—John S. Brusca
Assistant Examiner—Marjorie A. Moran
(74) Attorney, Agent, or Firm—Morgan, Lewis & Bockius LLP

(57) ABSTRACT

A preparation for oral administration which comprises S-(3-hydroxypropyl)-L-cysteine and one or more excipients, where the excipients do not cause discoloration of S-(3-hydroxypropyl)-L-cysteine is disclosled. According to an embodiment of the invention, the excipient may comprise a starch and/or a cyclodextrin. Typical starches used in the invention include corn starch, potato starch, wheat starch, and rice starch. Typical cyclodextrins used in the invention include α-cyclodextrin, β-cyclodextrin, and γ-cyclodextrin. Other excipients, such as saccharides, sugar alcohols and cellulose are not present in amounts that cause discoloration of the HPCY.

4 Claims, No Drawings

ORAL PREPARATIONS COMPRISING S-(3-HYDROXYPROPYL)-L-CYSTEINE

BACKGROUND OF THE INVENTION

1. Field of the Invention

The present invention relates to stable preparations for oral administration comprising S-(3-hydroxypropyl)-L-cysteine useful as an expectorant.

2. Background Art

It has been reported that S-(3-hydroxypropyl)-L-cysteine (hereinafter referred to as "HPCY") is useful as an expectorant (JP-A-2-3674; the term "JP-A" as used herein means an "unexamined published Japanese patent application"). Examples of the dosage form of HPCY include oral administration preparations, such as tablets, capsules, powders, granules, troches, solutions, and the like; and parenteral administration preparations, such as subcutaneous, intramuscular or intravenous injections, transfusion admixtures, suppositories, and the like. Among these, oral solid preparations are recommendable because of simple handling and easy administration.

HPCY is a compound having excellent stability, because it hardly causes discoloration in the presence of moisture or in the air when it is present alone. However, the discoloration occurs when it is used together with additives which are frequently used in the production of solid preparations, such as various saccharides, sugar alcohols, celluloses, and the like.

Since not only such a discoloration spoils the appearance of medicines but also it sometimes causes reduction of the content, the discoloration should be avoided.

Although there are many means for preventing discoloration of medicines, the countermeasure varies depending on the cause. For example, if moisture is the cause of discoloration, the moisture content of each preparation is reduced by drying or the preparation is blocked from the outside by coating or through a proper design of its packing. Also, if the cause is oxidation reaction, addition of an antioxidant is effective. However, discoloration is generally influenced by the coexisting components and preservation environments in a complicated manner, so that the real cause is not clear in many cases.

SUMMARY OF THE INVENTION

An object of the present invention is to provide an HPCY-containing solid preparation for oral administration which hardly causes discoloration even after a long period of storage due to a pharmaceutical means.

Accordingly, the present invention provides a preparation for oral administration which comprises S-(3-hydroxypropyl)-L-cysteine and an excipient, wherein the excipient is substantially only starch.

Also, the present invention provides a preparation for oral administration which comprises S-(3-hydroxypropyl)-L-cysteine and a cyclodextrin.

DETAILED DESCRIPTION OF THE INVENTION

The present inventors have conducted intensive studies and found as a result of the efforts that a stable oral preparation which causes less discoloration even after a long period of storage can be obtained when HPCY is blended as an excipient with substantially only starch or a cyclodextrin. The present invention has been accomplished on the basis of this finding.

According to the first embodiment of the present invention, substantially only starch should be used as an excipient, because it is not preferred that blending of other excipients excluding cyclodextrins, such as saccharides, sugar alcohols, celluloses, and the like, will cause discoloration.

In the present invention, the expression "the excipient is substantially only starch" means that the excipient is starches alone or that other excipients excluding cyclodextrins are present in such an amount that discoloration of the preparation for oral administration of the present invention is not caused. Preferably, the starches are present in an amount of 90 to 100% by weight of the total excipients.

Examples of the starches for use in the present invention include corn starch, potato starch, wheat starch, rice starch, and the like. These starches may be used alone or as a mixture of two or more. The amount used of these starches is not particularly limited; however, they are preferably used in an amount of 0.01 to 8 parts by weight, more preferably 0.02 to 4 parts by weight, based on 1 part by weight of HPCY.

Furthermore, examples of the cyclodextrins for use in the present invention include α-cyclodextrin, β-cyclodextrin, and γ-cyclodextrin. These cyclodextrins may be used alone or as a mixture of two or more. The amount used of these cyclodextrins is not particularly limited; however, they are preferably used in an amount of 0.01 to 8 parts by weight, more preferably 0.02 to 4 parts by weight, based on 1 part by weight of HPCY.

When these cyclodextrins are used, other excipients may also be used or the above-described starches may be used as excipients. If the starches coexists, stable preparations can be obtained in any mixing ratios of the cyclodextrins and the starches.

When the preparation for oral administration of the present invention is produced, HPCY is mixed with starches and/or cyclodextrins and, as occasion demands, additives usually used in the production of medicines, and the resulting mixture is made into oral preparations, such as tablets, capsules, powders, granules, troches, and the like, in the conventional way. The conventionally used additives may be selected optionally from correctives, flavors, binders, lubricants, and the like, with the proviso that they do not cause discoloration when coexisted with HPCY. Preferably, these additives are used in an amount of 5% by weight or less, more preferably 2% by weight or less, of the total amount of the preparation.

Examples of the present invention are given below by way of illustration and not by way of limitation.

EXAMPLE 1

After adding 78 parts by weight of corn starch, 1 part by weight of talc and 1 part by weight of magnesium stearate to 200 parts by weight of HPCY, the resulting mixture was mixed using a V-type mixer to obtain a powder for tablet making use. Using a rotary tablet machine (manufactured by Kikusui Seisakusho), the thus obtained powder for tablet making use was made into tablets, each tablet having a diameter of 8.5 mm and a weight of 280 mg.

EXAMPLE 2

After adding 18 parts by weight of corn starch, 1 part by weight of talc and 1 part by weight of magnesium stearate to 200 parts by weight of HPCY, the resulting mixture was mixed using a V-type mixer to obtain a powder for tablet making use. Using a rotary tablet machine, the thus obtained powder for tablet making use was made into tablets, each tablet having 8 mm in diameter and 220 mg in weight.

EXAMPLE 3

After adding 78 parts by weight of α-cyclodextrin, 1 part by weight of talc and 1 part by weight of magnesium stearate to 200 parts by weight of HPCY, tablets of 280 mg per tablet were produced in the same manner as in Example 1.

EXAMPLE 4

After adding 18 parts by weight of α-cyclodextrin, 1 part by weight of talc and 1 part by weight of magnesium stearate to 200 parts by weight of HPCY, tablets of 220 mg per tablet were produced in the same manner as in Example 2.

EXAMPLE 5

One part by weight of HPCY was mixed with 1 part by weight of corn starch, and the mixture was packed in capsules.

EXAMPLE 6

One part by weight of HPCY was mixed with 1 part by weight of a-cyclodextrin, and the mixture was packed in capsules.

EXAMPLE 7 to 11

Powders were produced by mixing HPCY with potato starch at different ratios shown in Table 1.

TABLE 1

| Example | 7 | 8 | 9 | 10 | 11 |
|---|---|---|---|---|---|
| HPCY | 100 | 50 | 1 | 1 | 1 |
| Potato starch | 1 | 1 | 1 | 4 | 8 |

EXAMPLES 12 to 16

Powders were produced by mixing HPCY with α-cyclodextrin at different ratios shown in Table 2.

TABLE 2

|  | 12 | 13 | 14 | 15 | 16 |
|---|---|---|---|---|---|
| HPCY | 100 | 50 | 1 | 1 | 1 |
| α-Cyclodextrin | 1 | 1 | 1 | 4 | 8 |

Comparative Example 1

After adding 16 parts by weight of lactose, 2 parts by weight of hydroxypropylcellulose, 1 part by weight of talc and 1 part by weight of magnesium stearate to 200 parts by weight of HPCY, the resulting mixture was mixed using a V-type mixer to obtain a powder for tablet making use. Using a rotary tablet machine, the thus obtained powder for tablet making use was made into tablets, each tablet having a diameter of 8 mm and a weight of 220 mg.

Comparative Example 2

Powders were produced by mixing 400 parts by weight of HPCY with 390 parts by weight of lactose and 10 parts by weight of hydroxypropylcellulose.

Comparative Example 3

Powders were produced by mixing 400 parts by weight of HPCY with 380 parts by weight of lactose and 20 parts by weight of corn starch.

Comparative Example 4

Tablets were produced by mixing 200 parts by weight of HPCY with 28 parts by weight of lactose, 20 parts by weight of corn starch, 1 part by weight of talc and 1 part by weight of magnesium stearate.

Test Example 1

The preparations produced in Examples 1 to 16 and Comparative Examples 1 to 4 were stored at room temperature for 12 months, at 40° C. for 3 months or at 50° C. for 1 month to observe their discoloration. The results are shown in Table 3.

TABLE 3

|  | 12 Months at Room Temperature | 3 Months at 40° C. | 1 Month at 50° C. |
|---|---|---|---|
| Ex. 1 | − | − | − |
| Ex. 2 | − | − | − |
| Ex. 3 | − | − | − |
| Ex. 4 | − | − | − |
| Ex. 5 | − | − | − |
| Ex. 6 | − | − | − |
| Ex. 7 | − | − | − |
| Ex. 8 | − | − | − |
| Ex. 9 | − | − | − |
| Ex. 10 | − | − | − |
| Ex. 11 | − | − | − |
| Ex. 12 | − | − | − |
| Ex. 13 | − | − | − |
| Ex. 14 | − | − | − |
| Ex. 15 | − | − | − |
| Ex. 16 | − | − | − |
| Comp. Ex. 1 | ± | + | ++ |
| Comp. Ex. 2 | ± | ± | + |
| Comp. Ex. 3 | — | — | + |
| Comp. Ex. 4 | — | — | + |

−:no discoloration
±:slight discoloration
+:discoloration
++:accelerated discoloration Thus, as apparent from the results shown in Table 3, the HPCY-containing preparations of the present invention are excellent in quality, because they hardly cause discoloration even after a prolonged period of storage.

While the invention has been described in detail and with reference to specific embodiments thereof, it will be apparent to one skilled in the art that various changes and modifications can be made therein without departing from the spirit and scope thereof.

What is claimed is:

1. An oral preparation comprising an active ingredient, an excipient, and an additive, wherein:
   the active ingredient consists essentially of S-(3-hydroxypropyl)-L-cysteine (HPCY), the excipient is corn starch, and the additive comprises talc and magnesium stearate,
   in the amounts of 200 parts by weight of HPCY, 78 parts by weight of corn starch, 1 part by weight of talc, and 1 part by weight of magnesium stearate, whereby the oral preparation is not discolored after 12 months at room temperature, or 3 months at 40° C., or 1 month at 50° C.

2. An oral preparation comprising an active ingredient, an excipient, and an additive, wherein:
   the active ingredient consists essentially of S-(3-hydroxypropyl)-L-cysteine (HPCY), the excipient is corn starch, and the additive comprises talc and magnesium stearate, in the amounts of 200 parts by weight of HPCY, 18 parts by weight of corn starch, 1 part by weight of talc, and 1 part by weight of magnesium stearate, whereby the oral preparation is not discolored after 12 months at room temperature, or 3 months at 40° C., or 1 month at 50° C.

3. An oral preparation comprising an active ingredient, an excipient, and an additive, wherein:

the active ingredient consists essentially of S-(3-hydroxypropyl)-L-cysteine (HPCY), the excipient is α-cyclodextrin, and the additive comprises talc and magnesium stearate, in the amounts of 200 parts by weight of HPCY, 78 parts by weight of α-cyclodextrin, 1 part weight of talc, and 1 part by weight of magnesium stearate, whereby the oral preparation is not discolored after 12 months at room temperature, or 3 months at 40° C., or 1 month at 50° C.

4. An oral preparation comprising an active ingredient, an excipient, and an additive, wherein:

the active ingredient consists essentially of S-(3-hydroxypropyl)-L-cysteine (HPCY), the excipient is α-cyclodextrin, and the additive comprises talc and magnesium stearate, in the amounts of 200 parts by weight of HPCY, 18 parts by weight of α-cyclodextrin, 1 part weight of talc, and 1 part by weight of magnesium stearate, whereby the oral preparation is not discolored after 12 months at room temperature, or 3 months at 40° C., or 1 month at 50° C.

* * * * *